United States Patent
Eisenacher et al.

(10) Patent No.: US 9,133,083 B2
(45) Date of Patent: Sep. 15, 2015

(54) CONTINUOUS METHOD FOR THE PRODUCTION OF NEOPENTYL GLYCOL

(71) Applicant: Oxea GmbH, Oberhausen (DE)

(72) Inventors: Matthias Eisenacher, Wesel (DE); Kurt Schalapski, Oberhausen (DE); Peter Heymanns, Essen (DE); Rainer Lukas, Essen (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/432,628

(22) PCT Filed: Sep. 30, 2013

(86) PCT No.: PCT/EP2013/002930
§ 371 (c)(1),
(2) Date: Mar. 31, 2015

(87) PCT Pub. No.: WO2014/067602
PCT Pub. Date: May 8, 2014

(65) Prior Publication Data
US 2015/0225319 A1    Aug. 13, 2015

(30) Foreign Application Priority Data
Oct. 29, 2012   (DE) .......................... 10 2012 021 276

(51) Int. Cl.
*C07C 29/141* (2006.01)
*B01J 23/889* (2006.01)

(52) U.S. Cl.
CPC .......... *C07C 29/141* (2013.01); *B01J 23/8892* (2013.01)

(58) Field of Classification Search
CPC ..................................................... C07C 29/141
See application file for complete search history.

(56) References Cited

U.S. PATENT DOCUMENTS

| | | |
|---|---|---|
| 3,340,312 A | 9/1967 | Duke et al. |
| 4,094,914 A | 6/1978 | Rottig et al. |
| 4,250,337 A | 2/1981 | zur Hausen et al. |
| 4,855,273 A * | 8/1989 | Pohl et al. ............. 502/244 |
| 4,855,515 A | 8/1989 | Morris et al. |
| 4,918,247 A | 4/1990 | Breitkopf et al. |
| 5,134,108 A * | 7/1992 | Thakur et al. ............ 502/318 |
| 5,146,012 A * | 9/1992 | Salek et al. ............. 568/881 |
| 8,357,824 B2 | 1/2013 | Schulz et al. |

FOREIGN PATENT DOCUMENTS

| | | |
|---|---|---|
| DE | 1518784 A1 | 8/1969 |
| DE | 10317545 A1 | 11/2004 |
| DE | 102008033163 A1 | 1/2010 |
| EP | 0006460 A1 | 1/1980 |
| EP | 0008767 A1 | 3/1980 |
| EP | 0278106 A1 | 8/1988 |
| EP | 0484800 A2 | 5/1992 |
| EP | 0522368 A1 | 1/1993 |
| GB | 2482887 A | 2/2012 |
| WO | 9829374 A1 | 7/1998 |
| WO | 2014067600 A1 | 5/2014 |

OTHER PUBLICATIONS

Kaddouri et al., Journal of Thermal Analysis and Calorimetry (1998), 53(2), pp. 533-545.*
Database CAPLUS in STN, Acc. No. 1995:747174, Rong et al., Shiyou Huagong (1995), 24(7), pp. 473-477 (abstract).*
Database CAPLUS in STN, Acc. No. 1994:582375, Oprescu et al., RO 102039 B1 (Mar. 30, 1992) (abstract).*
International Search Report dated Feb. 5, 2014.
International Preliminary Report on Patentability dated May 14, 2015.

* cited by examiner

*Primary Examiner* — Brian J Davis
(74) *Attorney, Agent, or Firm* — Michael W. Ferrell

(57) ABSTRACT

A continuous method for preparing neopentyl glycol by addition of isobutyraldehyde and formaldehyde in the presence of a tertiary alkylamine as catalyst to give hydroxypivaldehyde with subsequent hydrogenation in the gas phase at a temperature of 125 to 180° C., is characterized in that the hydrogenation is carried out in the presence of a copper chromite catalyst comprising the activators barium and manganese and at a superatmospheric pressure of 30 to 120 kPa.

20 Claims, No Drawings

CONTINUOUS METHOD FOR THE PRODUCTION OF NEOPENTYL GLYCOL

CLAIM FOR PRIORITY

This application is a national phase application of PCT/EP2013/002930 FILED Sep. 30, 2013 which was based on application DE 10 2012 021 276.3 FILED Oct. 29, 2012. The priorities of PCT/EP2013/002930 and DE 10 2012 021 276.3 are hereby claimed and their disclosures incorporated herein by reference.

TECHNICAL FIELD

The present invention relates to a continuous method for preparing neopentyl glycol by hydrogenation of hydroxypivaldehyde in the gas phase over barium- and manganese-doped copper chromite catalysts.

BACKGROUND

Polyhydric alcohols or polyols possess considerable economic significance as a condensation component for forming polyesters or polyurethanes, synthetic resin coatings, lubricants and plasticizers. In this context, polyhydric alcohols of interest are particularly those which are obtained by a mixed aldol addition of formaldehyde with iso- or n-butyraldehyde. The aldol addition between formaldehyde and the appropriate butyraldehyde first forms an aldehydic intermediate which then has to be reduced to the polyhydric alcohol. An industrially important polyhydric alcohol obtainable by this method is neopentyl glycol [NPG, 2,2-dimethylpropane-1,3-diol] formed from the mixed aldolisation of formaldehyde and isobutyraldehyde.

The aldol addition reaction is carried out in the presence of basic catalysts, for example alkali metal hydroxides or aliphatic amines, and initially affords the isolable hydroxypivaldehyde (HPA) intermediate. This intermediate can subsequently be converted with excess formaldehyde in accordance with the Cannizzaro reaction to neopentyl glycol to form one equivalent of a formate salt. In this configuration of the reduction step, the formate salt is therefore obtained as co-product and the cost-effectiveness of this method variant also depends on the commercial opportunities for the formate salt.

However, also implemented industrially is the catalytic hydrogenation of hydroxypivaldehyde in the gas and liquid phase over a metal catalyst. In the gas phase variant, hydroxypivaldehyde is initially freed from high boilers in an evaporator connected upstream of the hydrogenation stage. The subsequent hydrogenation is preferably conducted in the presence of Raney nickel catalysts or supported catalysts based on nickel which may additionally comprise further active metals such as copper or chromium and, additionally, activators. The gas phase variant is covered, for example, in EP 0 278 106 A1; U.S. Pat. No. 4,094,914; Ullmann's Encyclopedia of Industrial Chemistry, publisher VCH, 5$^{th}$ Ed., 1985, Vol. A1, p. 308; Chemiker-Zeitung (Chemist journal), volume 100, (1976), No. 12, pp. 504-514.

The hydrogenation in the liquid phase has been extensively described, for example in EP 0 484 800 A2, using catalysts based on copper, zinc and zirconium. The liquid phase hydrogenation of hydroxypivaldehyde is frequently conducted in the presence of copper chromite catalysts. Copper chromite catalysts frequently comprise other metals as activators, for example barium, cadmium, magnesium, manganese and/or a rare earth metal. According to U.S. Pat. No. 4,855,515, manganese-doped copper chromite catalysts in particular excel at the hydrogenation of the aldolisation product of the reaction of formaldehyde with isobutyraldehyde. WO98/29374 A1 discloses the use of a barium-doped copper chromite catalyst for the hydrogenation of hydroxypivaldehyde in a methanolic solution.

According to the teaching of DE 1 518 784 A1, a mixture of hydroxypivaldehyde and excess isobutyraldehyde is hydrogenated to neopentyl glycol and isobutanol in the presence of a copper chromite catalyst which has been doped with barium. According to EP 0 006 460 A1, the two-step high pressure hydrogenation of crude hydroxypivaldehyde, which is carried out with increasing hydrogenation temperatures, also uses a copper chromite catalyst activated with barium.

EP 0 522 368 A1 discloses carrying out the hydrogenation of hydroxypivaldehyde in a solution comprising at least 20% by weight of a low molecular weight alcohol, for example methanol or n-butanol, based on the mixture of alcohol and reaction product, and also water in an amount of not more than 40% by weight, based on the total amount of water, alcohol and reaction product. The hydrogenation catalyst recommended is a copper chromite catalyst.

As a product produced industrially, neopentyl glycol has a major economic significance and thus there always exists a need to improve the known methods for preparing neopentyl glycol, whether by improving the product yield, by better utilization of plant equipment or by a lowering of energy input.

SUMMARY OF INVENTION

It has surprisingly been found that neopentyl glycol may be prepared with high selectivity and yield by hydrogenation of hydroxypivaldehyde if the hydrogenation is conducted continuously in the gas phase in the presence of a copper chromite catalyst which has been doped both with manganese and with barium.

The present invention therefore relates to a continuous method for preparing neopentyl glycol by addition of isobutyraldehyde and formaldehyde in the presence of a tertiary alkylamine as catalyst to give hydroxypivaldehyde with subsequent hydrogenation in the gas phase at a temperature of 125 to 180° C., characterized in that the hydrogenation is carried out in the presence of a copper chromite catalyst comprising the activators barium and manganese and at a superatmospheric pressure of 30 to 120 kPa.

It was surprisingly found that with the use of copper chromite catalysts comprising barium and manganese as activators, and by setting a hydrogenation temperature of 125 to 180° C., preferably 140 to 180° C., the selective hydrogenation of hydroxypivaldehyde to neopentyl glycol is successful.

At excessively low hydrogenation temperatures the hydrogenation of hydroxypivaldehyde is incomplete. At excessively high temperatures an increased decomposition of the tertiary alkylamine used as the aldolization catalyst also occurs, which leads to secondary products that are difficult to remove and is therefore undesirable.

It is furthermore very surprising that the hydrogenation to neopentyl glycol is successful in high yield at an exceedingly low superatmospheric pressure of only 30 to 120 kPa. The method according to the invention therefore only requires a very low expenditure in terms of compressor output and is therefore very energy efficient.

DETAILED DESCRIPTION

The aldol addition of isobutyraldehyde and an aqueous formaldehyde solution is conducted in the presence of tertiary alkylamines as aldol addition catalyst, which may comprise the same or different alkyl groups and therefore may be symmetrically or asymmetrically composed, or in the presence of tertiary alkylamines having a plurality of trialkylamine functions. The reaction is conducted in the presence of, for example, trimethyl-, triethyl-, tri-n-propyl-, triisopropyl-, methyldiethyl-, methyldiisopropylamine, tri-n-butylamine, dimethyl-tert-butylamine or N,N'-tetramethyl-ethylenediamine. Trimethylamine, triethylamine, tri-n-propylamine and tri-n-butylamine have proven to be particularly suitable catalysts.

The aldehydes can be reacted in a molar ratio, but it is also possible to use one of the two reaction partners in excess. Formaldehyde is used in aqueous solution of which the formaldehyde content is typically 20 to 50% by weight. It has been found that the doped copper chromite catalyst used in the method according to the invention has a surprisingly high resistance to formaldehyde. Thus, in the aldol addition stage, molar ratios of formaldehyde to isobutyraldehyde of 1:1 can be adjusted in favour of formaldehyde, generally up to 1.2:1, preferably 1.1:1. By reducing the isobutyraldehyde input, the isobutanol formation in the hydrogenation stage is suppressed and the neopentyl glycol yield, based on isobutyraldehyde input, is increased.

The reaction between isobutyraldehyde and formaldehyde is conducted at temperatures between 20 and 100° C., advantageously from 80 to 95° C. Generally the reaction is carried out at standard pressure, but, superatmospheric pressure can also be used. The tertiary alkylamine used as the aldol addition catalyst is present in the reaction mixture in an amount of 1 to 20, preferably to 2 to 12 mol %, based on isobutyraldehyde.

In addition to the water from the aqueous formaldehyde solution and low amounts of methanol, which is also present in the aqueous formaldehyde solution, isobutanol is optionally added to the reaction mixture as diluent. The isobutanol addition is not strictly required, but if isobutanol is added, the content thereof in the reaction mixture is in the range of 15 to 30% by weight, preferably 15 to 25% by weight, based on the organic component in the total reaction mixture. Additional solvents and diluents are not required. The practical procedure for the addition reaction is conducted in a stirred tank, in a stirred tank cascade or in a reaction tube which may be charged with random packings or other internals to improve mixing of the reactants. The reaction proceeds exothermically and can be accelerated by heating.

The crude mixture resulting from the aldol addition, optionally following distillative or extractive removal of volatile constituents such as water, methanol, isobutanol and residual amounts of formaldehyde, isobutyraldehyde and of the aldolisation catalyst, or without prior removal, is placed in an evaporating device which is generally operated at temperatures of 140 to 190° C. at standard pressure. High boilers remain as a residue in the evaporator and are removed from the process.

The high boilers can be thermally recovered or, for example, be reductively cleaved separately according to the procedure according to DE 10 2008 033 163 A1. The high boilers are oxygen-containing compounds such as esters or cyclic acetals in which equivalents of neopentyl glycol are chemically bound. In the high boilers, the proportion is particularly high of mono- and diisobutyric esters of neopentyl glycol and also of the neopentyl glycol monohydroxypivalate disproportionation product formed from hydroxypivaldehyde by the Tishchenko reaction.

The volatile distillate from the evaporator essentially comprises hydroxypivaldehyde and, depending on the optional work-up of the crude aldol addition mixture, water, the diluent, if added, and further volatile components such as methanol from the formaldehyde stabilisation. Also present are residues entrained by the high boilers and the tertiary amine used as aldolisation catalyst. If the crude aldol addition mixture is placed in the evaporator without optional separation, the distillate generally comprises 15 to 30% by weight, preferably 15 to 25% by weight, of isobutanol, based on the organic component of the distillate.

In a preferred configuration of the invention, the water content in the distillate is adjusted to a value of 15 to 25% by weight, preferably 18 to 25% by weight, based on the total distillate, so that the subsequent hydrogenation stage is carried out in the presence of water at the amount established. The remainder, set to 100% by weight, is the organic component. The selective cleavage of the previously mentioned oxygen-containing high boilers to neopentyl glycol is improved in the subsequent hydrogenation step by the amount of water established in the preferred configuration of the invention. The water component also promotes advantageous heat distribution and advantageous dissipation of the heat of reaction during the hydrogenation step and reduces the danger of local temperature spikes occurring. In a procedure in which a distillate with a water content below 15% by weight is used and thus the hydrogenation is carried out in the presence of a lower amount of water, the advantageous effect on decreasing the high boiling component is distinctly less pronounced. In this case, it is recommended to specifically add water to give the required content. If the water content is too high, valuable reactor volume is unnecessarily occupied and not fully utilised.

The volatile distillate obtained is hydrogenated without further purification or workup steps.

The hydrogenation of the crude hydroxypivaldehyde is carried out at a temperature of 125 to 180° C., preferably 140 to 180° C., in the gas phase in the presence of barium- and manganese-doped copper chromite catalysts. The superatmospheric pressure is 30 to 120 kPa, preferably 60 to 100 kPa. Of particular proven worth is a reaction temperature of 140 to 180° C. and a superatmospheric pressure of 60 to 100 kPa. At lower superatmospheric pressures, satisfactory hydrogenation of hydroxypivaldehyde is no longer observed.

The hydrogenation of hydroxypivaldehyde is conducted in the presence of copper chromite catalysts which comprise barium and manganese as activators. Copper chromite catalysts may be described, according to H. Adkin, Org. React. 8, 1954, 1-27, as an equimolar combination of copper oxide and copper chromite, although they do not necessarily comprise copper chromite. Catalysts may be used either without carriers as unsupported catalysts or with carriers such as kieselguhr, silica gel or aluminium oxide as powders or in the form of tablets, stars, cylinders, rings or other particles of proportionately large surface area.

For the preparation, insoluble compounds of each of copper, chromium, manganese and barium are mixed, for example, in paste form and shaped into suitable bodies such as cylinders or tablets. After shaping, the latter are dried and calcined up to 500° C., wherein the solid compresses and the metals present are converted, if applicable, into the oxides.

It is also advantageous to start with aqueous solutions from which the solute is precipitated. Following filtration, the solid is dried and calcined up to 500° C., as with solid mixtures. Subsequently, it may be advisable to stir the solid in a low molecular weight organic acid such as formic acid, acetic acid, propionic acid or n-butyric acid in order to remove soluble constituents, then to wash until free of acid, to dry again and to calcine up to 500° C.

Following addition of additives such as graphite or alkali metal soaps or alkaline earth metal soaps, shaped bodies such as tablets or rings can then be produced.

The barium- and manganese-doped copper chromite catalysts comprise from 0.5 to 8% by weight, preferably from 3 to 5% by weight of manganese and from 0.5 to 8% by weight, preferably from 1 to 4% by weight of barium, in each case based on the total content of copper, chromium, barium and manganese. Of particularly proven value is a barium content in a range from 1 to 4% by weight and a manganese content in a range from 3 to 5% by weight, in each case based on the total content of copper, chromium, barium and manganese. In addition to the activators mentioned, further activators such as cadmium, magnesium, strontium and/or a rare earth metal can optionally be present.

The present invention thus also relates to a copper chromite catalyst comprising barium in an amount of 0.5 to 8% by weight and manganese in an amount of 0.5 to 8% by weight, in each case based on the total content of copper, chromium, barium and manganese.

The hydrogenation is carried out continuously in the gas phase, for example over fixedly arranged catalysts or in a fluidised bed over fluidised catalysts.

In the continuous mode, a catalyst hourly space velocity V/Vh, expressed in throughput volume per unit catalyst volume and time, of 0.2 to 2.0 $h^{-1}$, preferably 0.3 to 1.0 $h^{-1}$, has proven to be advantageous.

A higher hourly space velocity for the copper chromite catalyst is to be avoided since the hydroxypivaldehyde starting compound is then no longer completely hydrogenated and increased by-product formation is observed.

The hydrogenation is preferably carried out continuously in the gas phase in straight pass. A cycle gas mode is also possible, in which case a ratio of cycle gas stream to fresh gas stream of 40 to 70 has proven to be advantageous.

The hydrogenation is preferably carried out with pure hydrogen. Mixtures however may also be used comprising free hydrogen and, in addition, constituents inert under the hydrogenation conditions.

The pure neopentyl glycol is obtained from the hydrogenated reaction mixture by following conventional distillation methods. Solvents or diluents removed in this process may be fed back again into the aldol addition stage.

The hydrogenation method according to the invention converts hydroxypivaldehyde to neopentyl glycol with a high conversion and high selectivity. The very low superatmospheric pressure in the hydrogenation is notable.

The cleavage of the tertiary alkylamine into volatile, nitrogen-containing compounds, which lead to undesirable impurities and which are difficult to remove in the subsequent distillative work-up and which interfere during the further work-up of neopentyl glycol, is suppressed.

The method according to the invention is further illustrated by means of some examples which follow.

EXAMPLES

Example 1

Preparation of a Manganese- and Barium-Doped Copper Chromite Catalyst 2.8 kg of copper nitrate trihydrate, 400 g of manganese nitrate in the form of a 50% solution in dilute nitric acid and 150 g of barium nitrate were dissolved in 20 liters of water at 55° C. Separately, 2.6 kg of ammonium dichromate were dissolved in 12 liters of water and 4 liters of 25% ammonia solution. The ammonium dichromate solution was then slowly added dropwise to the copper nitrate solution. A red-brown solid precipitated. To complete the precipitation, the mixture was further stirred for one hour and cooled to room temperature. The solid was then filtered off and dried at 110° C. in a drying cabinet. The dried solid was calcined at 350° C. over 4 hours at a heating rate of 2° C./min. Following the calcination and cooling of the solid, it was stirred with 20 liters of 10% acetic acid. The solid was then washed free of acid with water and again dried at 110° C. and calcined at 350° C. at a heating rate of 2° C./min. The solid obtained in this form was used as catalyst. Based on the metals, the catalyst had the following composition: 47.5% copper, 46.5% chromium, 4.0% manganese, 2.0% barium.

Example 2

Use of the Catalyst from Example 1 as Fixed-Bed Catalyst

The catalyst from example 1 was mixed with 3% graphite and formed into 5×5 mm tablets. The tabletted catalyst was loaded into a 2.5 liter tube reactor and then activated in three stages under the following conditions:
Heating rate: 20° C./h to 180° C.
Nitrogen feed: 1000 l (STP)/h
Hydrogen feed: 20 l (STP)/h
Duration: 12 hours
Nitrogen feed: 1000 l (STP)/h
Hydrogen feed: 60 l (STP)/h
Duration: 6 hours
Nitrogen feed: 1000 l (STP)/h
Hydrogen feed: 120 l (STP)/h
Duration: 6 hours l (STP)=standard liter, 1 liter gas volume at a temperature of 20° C. and a pressure of 100 kPa.

To test the catalytic activity of the copper chromite catalysts prepared according to example 1, a crude hydroxypivaldehyde solution was used which had been prepared by the aldol reaction of isobutyraldehyde with formaldehyde with tri-n-propylamine catalysis. The crude mixture was placed in an evaporator operated at 150° C. and at standard pressure. The volatile distillate had the following composition and was fed continuously, without further purification together with hydrogen, into the top of the tube reactor in the hydrogenation stage:

Composition of the hydrogenation starting mixture, data in percent

| | |
|---|---|
| Formaldehyde | 0.9 |
| Isobutyraldehyde | 1.0 |
| Tri-n-propylamine | 7.0 |
| Isobutanol | 14.5 |
| hydroxypivaldehyde | 48.2 |
| Neopentyl glycol | 1.6 |
| Tishchenko ester | 2.7 |
| Water | 24.1 |

Tishchenko ester: neopentyl glycol monohydroxypivalate

The hydrogenation material was removed from the bottom of the tube reactor, piped into a high-pressure separator and hence into a non-pressurised vessel via a level control. The hydrogenation temperature and the catalyst hourly space velocity were adjusted according to the conditions in Table 1 below. All experiments were conducted at 80 kPa superatmospheric pressure.

Conversion and selectivity were determined by means of the following formulae:

Conversion=((Amount of hydroxypivaldehyde in the starting mixture−amount of hydroxypivaldehyde after hydrogenation)/Amount of hydroxypivaldehyde in the starting mixture)*100

Selectivity=(Amount of neopentyl glycol after hydrogenation/(Amount of hydroxypivaldehyde in the starting mixture−amount of hydroxypivaldehyde after hydrogenation))*100

TABLE 1

Continuous gas phase hydrogenation of hydroxypivaldehyde over barium- and manganese-doped copper chromite catalyst according to example 1

| Temperature/° C. | V/Vh/ $h^{-1}$ | Hydroxypivaldehyde conversion/% | Selectivity for neopentyl glycol/% |
|---|---|---|---|
| 161 | 0.29 | 99.9 | 97.3 |
| 163 | 0.48 | 99.9 | 98.2 |
| 155 | 0.57 | 99.8 | 98.6 |

As the experimental results show, the continuous gas phase hydrogenation of hydroxypivaldehyde in the presence of a barium- and manganese-doped copper chromite catalyst provides excellent results with respect to conversion and selectivity for neopentyl glycol.

Example 3

Investigation of the Formaldehyde Tolerance of the Catalyst from Example 1

The experimental setup was used as in example 2. By specific addition of a 40% aqueous formaldehyde solution, starting mixtures with the following composition were obtained, which were then hydrogenated at 155° C., 80 kPa superatmospheric pressure and a V/Vh of 0.3 $h^{-1}$ (data in percent).

| Starting mixture | 1 | 2 | 3 |
|---|---|---|---|
| Formaldehyde | 1.4 | 0.9 | 1.1 |
| Isobutyraldehyde | 1.0 | 1.0 | 0.7 |
| Tri-n-propylamine | 7.0 | 7.0 | 6.1 |
| Isobutanol | 14.4 | 14.5 | 15.0 |
| Hydroxypivaldehyde | 48.1 | 48.2 | 48.2 |
| Neopentyl glycol | 1.6 | 1.6 | 1.8 |
| Tishchenko ester | 2.8 | 2.7 | 2.9 |
| Water | 23.7 | 24.1 | 24.2 |

The following results were obtained:

| Starting mixture | Hydroxypivaldehyde conversion/% | Selectivity for neopentyl glycol/% |
|---|---|---|
| 1 | 99.8 | 98.5 |
| 2 | 99.8 | 98.2 |
| 3 | 99.9 | 97.8 |

The invention claimed is:

1. Continuous method for preparing neopentyl glycol by addition of isobutyraldehyde and formaldehyde in the presence of a tertiary alkylamine as catalyst to give hydroxypivaldehyde with subsequent hydrogenation in the gas phase at a temperature of 125 to 180° C., characterized in that the hydrogenation is carried out in the presence of a copper chromite catalyst comprising the activators barium and manganese and at a superatmospheric pressure of 30 to 120 kPa.

2. Method according to claim 1, characterized in that the hydrogenation is carried out in the presence of water in an amount of 15 to 25% by weight based on the total amount of the hydrogenation starting mixture used.

3. Method according to claim 1, characterized in that the hydrogenation is carried out at a temperature of 140 to 180° C. and a superatmospheric pressure of 60 to 100 kPa.

4. Method according to claim 1, characterized in that the tertiary alkylamines used are symmetrical tertiary alkylamines.

5. Method according to claim 4, characterized in that the symmetrical tertiary alkylamines used are trimethylamine, triethylamine, tri-n-propylamine or tri-n-butylamine.

6. Method according to claim 1, characterized in that the tertiary alkylamines used are asymmetrical tertiary alkylamines.

7. Method according to claim 1, characterized in that the copper chromite catalyst comprises barium in an amount of 0.5 to 8% by weight and manganese in an amount of 0.5 to 8% by weight, in each case based on the total content of copper, chromium, barium and manganese.

8. Method according to claim 7, characterized in that the copper chromite catalyst comprises barium in an amount of 1 to 4% by weight and manganese in an amount of 3 to 5% by weight, in each case based on the total content of copper, chromium, barium and manganese.

9. Method according to claim 1, characterized in that the continuous gas phase hydrogenation is carried out in a cycle gas mode with a cycle gas stream and a fresh gas stream at a ratio of cycle gas stream to fresh gas stream of 40 to 70.

10. Copper chromite catalyst comprising barium in an amount of 0.5 to 0.8% by weight and manganese in an amount of 0.5 to 8% by weight, in each case based on the total content of copper, chromium, barium and manganese.

11. Method according to claim 1, characterized in that the hydrogenation is carried out in the presence of water in an amount of 18 to 25% by weight, based on the total amount of the hydrogenation starting mixture used.

12. Method according to claim 2, characterized in that the hydrogenation is carried out at a temperature of 140 to 180° C. and a superatmospheric pressure of 60 to 100 kPa.

13. Method according to claim 2, characterized in that the tertiary alkylamines used are symmetrical tertiary alkylamines.

14. Method according to claim 3, characterized in that the tertiary alkylamines used are symmetrical tertiary alkylamines.

15. Method according to claim 13, characterized in that the symmetrical tertiary alkylamines used are trimethylamine, triethylamine, tri-n-propylamine or tri-n-butylamine.

16. Method according to claim 14, characterized in that the symmetrical tertiary alkylamines used are trimethylamine, triethylamine, tri-n-propylamine or tri-n-butylamine.

17. Method according to claim 2, characterized in that the tertiary alkylamines used are asymmetrical tertiary alkylamines.

18. Method according to claim 3, characterized in that the tertiary alkylamines used are asymmetrical tertiary alkylamines.

19. Method according to claim 2, characterized in that the copper chromite catalyst comprises barium in an amount of 0.5 to 8% by weight and manganese in an amount of 0.5 to 8% by weight, in each case based on the total content of copper, chromium, barium and manganese.

20. Method according to claim 3, characterized in that the copper chromite catalyst comprises barium in an amount of 0.5 to 8% by weight and manganese in an amount of 0.5 to 8% by weight, in each case based on the total content of copper, chromium, barium and manganese.

\* \* \* \* \*